(12) United States Patent
Skubitz et al.

(10) Patent No.: US 6,506,211 B1
(45) Date of Patent: *Jan. 14, 2003

(54) STENT DESIGNS

(75) Inventors: Sean P. Skubitz, Shoreview, MN (US); Burns P. Doran, Albertville, MN (US)

(73) Assignee: Scimed Life Systems, Inc., Maple Grove, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 14 days.

(21) Appl. No.: 09/681,006

(22) Filed: Nov. 13, 2000

(51) Int. Cl.$^7$ .................................................. A61F 2/06
(52) U.S. Cl. ...................................................... 623/1.15
(58) Field of Search ................................ 623/1.11, 1.12, 623/1.13, 1.14, 1.15, 1.16, 1.17, 1.18, 1.19, 1.2, 1.21, 1.22; 606/108, 191, 192, 194, 195, 198

(56) References Cited

U.S. PATENT DOCUMENTS

| | | | | |
|---|---|---|---|---|
| 5,019,090 A | | 5/1991 | Pinchuk | 606/194 |
| 5,116,365 A | | 5/1992 | Hillstead | 623/1 |
| 5,161,547 A | | 11/1992 | Tower | 128/898 |
| 5,549,663 A | | 8/1996 | Cottone, Jr. | 623/1 |
| 5,630,829 A | | 5/1997 | Lauterjung | 606/198 |
| 5,697,971 A | | 12/1997 | Fischell et al. | 623/1 |
| 5,716,396 A | | 2/1998 | Williams, Jr. | 623/1 |
| 5,741,327 A | * | 4/1998 | Frantzen | 623/1 |
| 5,755,770 A | | 5/1998 | Ravenscroft | 623/1 |
| 5,755,781 A | | 5/1998 | Jayaraman | 623/1 |
| 5,810,872 A | | 9/1998 | Kanesaka et al. | 606/198 |
| 5,824,046 A | | 10/1998 | Smith et al. | 623/1 |
| 5,897,589 A | | 4/1999 | Cottenceau et al. | 623/1 |
| 5,913,897 A | | 6/1999 | Corso, Jr. et al. | 623/1 |
| 5,935,162 A | | 8/1999 | Dang | 623/1 |
| 5,957,930 A | | 9/1999 | Vrba | 606/108 |
| 6,013,091 A | | 1/2000 | Ley et al. | 606/191 |
| 6,017,365 A | * | 1/2000 | Von Oepen | 623/1 |
| 6,022,370 A | | 2/2000 | Tower | 606/194 |
| 6,033,433 A | * | 3/2000 | Her et al. | 623/1 |
| 6,042,597 A | | 3/2000 | Kveen et al. | 606/198 |
| 6,117,165 A | | 9/2000 | Becker | 623/1 |
| 6,120,522 A | | 9/2000 | Vrba et al. | 606/190 |
| 6,123,712 A | | 9/2000 | DiCaprio et al. | 606/108 |
| 6,190,403 B1 | * | 2/2001 | Fischell et al. | 623/1 |
| 6,206,911 B1 | * | 3/2001 | Milo | 623/1.15 |

FOREIGN PATENT DOCUMENTS

WO  99/44543  9/1999

OTHER PUBLICATIONS

U.S. patent application Ser. No. 09/261,687, filed Mar. 3, 1999, Ley et al.
U.S. patent appplication Ser. No. 08/511,076, filed Aug. 3, 1995, Brown et al.
U.S. patent appplication Ser. No. 09/197,278, filed Nov. 20, 1998, Brown et al.

* cited by examiner

Primary Examiner—David O. Reip
Assistant Examiner—Vy Q. Bui
(74) Attorney, Agent, or Firm—Vidas, Arrett & Steinkraus

(57) ABSTRACT

A stent may be constructed comprising a plurality of interconnected circumferential bands each bands comprising a plurality of concave and/or convex M-shaped segments joined together by loops.

16 Claims, 9 Drawing Sheets

STENT DESIGNS

BACKGROUND OF INVENTION

The use of stents in bodily lumen is well known. A stent is typically delivered in an unexpanded state to a desired location in a bodily lumen and then expanded.

The stent may be expanded via the use of mechanical device such as a balloon or the stent may be self-expanding.

Because a stent often must be delivered through tortuous anatomy, it is desirable for the stent to be flexible. It is also desirable for the stent to exhibit high scaffolding strength in the expanded state. In general, however, as stent flexibility is increased, scaffolding strength is decreased and similarly, as scaffolding strength is increased, flexibility is decreased.

There remains a need for a stent having a high degree of flexibility in the unexpanded state and high scaffolding strength in the expanded state.

All U.S. patents and applications and all other published documents mentioned anywhere in this application are incorporated herein by reference in their entirety.

The invention in various of its embodiment is summarized below. Additional details of the invention and/or additional embodiments of the invention may be found in the Detailed Description of the Invention below.

SUMMARY OF INVENTION

In one embodiment, the invention is directed to a stent comprising a plurality of interconnected circumferential bands with a flowpath therethrough. At least one of the bands includes at least one substantially M-shaped segment selected from the group consisting of convex M-shaped segments and concave M-shaped segments. In the case of a convex M-shaped segment, the segment comprises a first convex outer leg, a second convex outer leg and a connector connecting the first convex outer leg and the second convex outer leg. In the case of a concave M-shaped segment, the segment comprises a first concave outer leg, a second concave outer leg and a connector connecting the first concave outer leg and the second concave outer leg.

Desirably, the at least one band comprises a plurality of M-shaped segments whether convex, concave or both. Where present, adjacent convex M-shaped segments may be interconnected via a loop extending therebetween. The loop may optionally comprise a concave first portion and a concave second portion. Where present, adjacent concave M-shaped segments may be interconnected via a loop extending therebetween. The loop may optionally comprise a convex first portion and a convex second portion. Where convex M-shaped segments are present in multiple bands, they may optionally be inverted relative to one another in adjacent bands. Similarly, where concave M-shaped segments are present in multiple bands, they may optionally be inverted relative to one another in adjacent; bands.

In another embodiment, the invention is directed to a stent comprising a plurality of connected bands. At least one of the bands comprises a repeating pattern of three or more substantially parallel interconnected segments with a first curvature and three or more substantially parallel interconnected segments with a second curvature. One of the segments with the first curvature is connected to one of the segments with the second curvature. Desirably, the first curvature is opposite to the second curvature. Also desirably, the stent comprises a plurality of the bands with each band comprising a repeating pattern of three or more substantially parallel interconnected segments with a first curvature and three or more substantially parallel interconnected segments with a second curvature, one of the segments of the first curvature connected to one of the segments with the second curvature.

In another embodiment, the invention is directed to a stent comprising a plurality of interconnected circumferential bands where at least one of the bands has a proximal end and a distal end and one of the proximal and distal ends comprises at least one first loop and at least one second loop. The first loop includes a portion which is disposed substantially circumferentially and the second loop includes a portion which is substantially arrow shaped. Desirably, at least one of the bands comprises a plurality of first and second loops alternating with one another. Also desirably, the stent comprises a plurality of such bands. Adjacent bands may be connected one to the other to form combined bands with openings therein.

The invention is also directed to a stent comprising at least one first cell having a first end and a second end. The first end terminates in a circumferential component and the second end terminates in an arrow-shaped component opposite the first end. The stent may comprise a plurality of such interconnected first cells. Desirably, the first cells are interconnected circumferentially about the stent and/or longitudinally along the length of the stent.

In another embodiment, the invention is directed to a stent comprising a plurality of serpentine bands extending in a longitudinal direction, including a first serpentine band and a second serpentine band. The first and second serpentine bands are connected by at least one loop member and desirably a plurality of loop members extending in a direction non-parallel to the longitudinal axis of the stent. All or some of the longitudinally adjacent first loop members may open toward the proximal end of the stent. Optionally, longitudinally adjacent first loop members may be oppositely oriented about the longitudinal axis of the stent.. The stent may comprise additional serpentine bands extending in a longitudinal direction and connected to adjacent serpentine bands via additional first loop members.

In another embodiment, the invention is directed to a stent comprising at least one first cell comprising a first generally longitudinal sidewall having at least one bend therein, a second generally longitudinal sidewall having at least one bend therein, wherein the first generally longitudinal sidewall is substantially parallel to the second generally longitudinal sidewall, a proximal wall having at least one loop therein, the loop oriented non-parallel to the longitudinal axis of the stent and a distal wall having at least one loop therein, the loop oriented non-parallel to the longitudinal axis of the stent. Desirably, the stent comprises a plurality of such cells arranged longitudinally and/or circumferentially about the stent. All of the loops in the proximal walls of the cells and all of the loops in the distal walls of the cells may be substantially parallel to one another or may be non-parallel to one another.

In another embodiment, the invention is directed to a stent comprising a plurality of bands, where each band comprises a plurality of distally directed loops and a plurality of proximally directed loops. Each distally directed loop has an open end and a closed end and each proximally directed loop has an open end and a closed end. The proximally directed loops and the distally directed loops are non-parallel to the longitudinal axis of the stent and alternate around the band. Optionally, the proximally directed loops and the distally directed loops may be parallel to one another. Circumferentially adjacent proximally directed loops and distally directed loops are connected to one another by first connectors which extend from the open end of the proximally directed loops to the open end of the distally directed loops. The first connectors include a circumferential component. Bands which are adjacent one another are connected by one or more second connectors extending therebetween. The second connectors desirably have at least one bend therein.

in another embodiment, the invention is directed to a stent defined by a structure comprising a plurality of serpentine portions. Each serpentine portion has at least one peak and one trough. At least some of the serpentine portions advance discontinuously in a helical path about a longitudinal axis of the stent to form a discontinuous helical band. The serpentine portions may also be arranged such that at least some of the serpentine portions advance discontinuously in a substantially longitudinal path about a longitudinal axis of the stent to form a discontinuous band extending substantially in a lengthwise direction. Desirably, each of the serpentine portions forming the discontinuous band consists of one peak and one trough where the peak and trough are disposed at a non-zero angle with respect to the longitudinal axis of the stent. Also desirably, the serpentine portions may be arranged to form a plurality of discontinuous helical bands or discontinuous bands extending substantially in a lengthwise direction. All of the serpentine portions may be connected so as to form a continuous path extending from one end of the stent to the other end of the stent.

In yet another embodiment, the invention is directed to a stent comprising a meandering path of connected serpentine portions, each serpentine portion comprising first and second loop portions which are arranged side-by-side and have a side in common. The first and second loop portions each open in a non-longitudinal direction. Adjacent serpentine portions along the meandering path are connected by a connector having a longitudinal component and a circumferential component. Furthermore, adjacent serpentine portions along the meandering path are displaced longitudinally and circumferentially from one another. The serpentine portions may be arranged in at least one discontinuous band extending in a substantially longitudinal direction or the discontinuous band may extend substantially helically about a longitudinal axis of the stent. Desirably, each serpentine portion consists of a first loop and a second loop.

The invention is also directed to a stent comprising a meandering, substantially helical path of connected serpentine portions where each serpentine portion comprises first and second loop portions which are arranged side-by-side and have a side in common. The first and second loop portions each open in a non-longitudinal direction. The serpentine portions may optionally be arranged in at least one discontinuous band extending in a substantially longitudinal direction or in at least one discontinuous band extending substantially helically about a longitudinal axis of the stent.

The invention is further directed to a stent comprising at least one and desirably a plurality of omega building blocks. The omega building block comprises a circumferentially oriented omega-shaped loop, a substantially proximally oriented first lobe extending from the proximal end of the omega-shaped loop and a substantially distally oriented first lobe extending from the distal end of the omega-shaped loop. Where a plurality of omega building blocks are present, the omega building blocks are desirably arranged in one or more bands extending in a lengthwise direction. Longitudinally adjacent omega building blocks in the band extending in a lengthwise direction are connected by dual lobe members. Each dual lobe member comprises a substantially proximally oriented second lobe and a substantially distally oriented second lobe connected to the substantially proximally oriented second lobe. The substantially proximally oriented second lobe is at the proximal end of the dual lobe member and the substantially distally oriented second lobe is at the distal end of the dual lobe member. The substantially distally oriented first lobe of an omega building block is arranged side by side and has a side in common with the substantially proximally oriented second lobe of a dual lobe member and the substantially proximally oriented first lobe of a longitudinally adjacent omega building block is arranged side by side and has a side in common with the substantially distally oriented second lobe of the dual lobe member. At least one and desirably a plurality and more desirably all of the omega shaped loops are connected circumferentially to circumferentially adjacent dual lobe members between the substantially proximally oriented second lobe and the substantially distally oriented second lobe.

DETAILED DESCRIPTION

While this invention may be embodied in many different forms, there are described in detail herein specific preferred embodiments of the invention. This description is an exemplification of the principles of the invention and is not intended to limit the invention to the particular embodiments illustrated.

Figure 1:
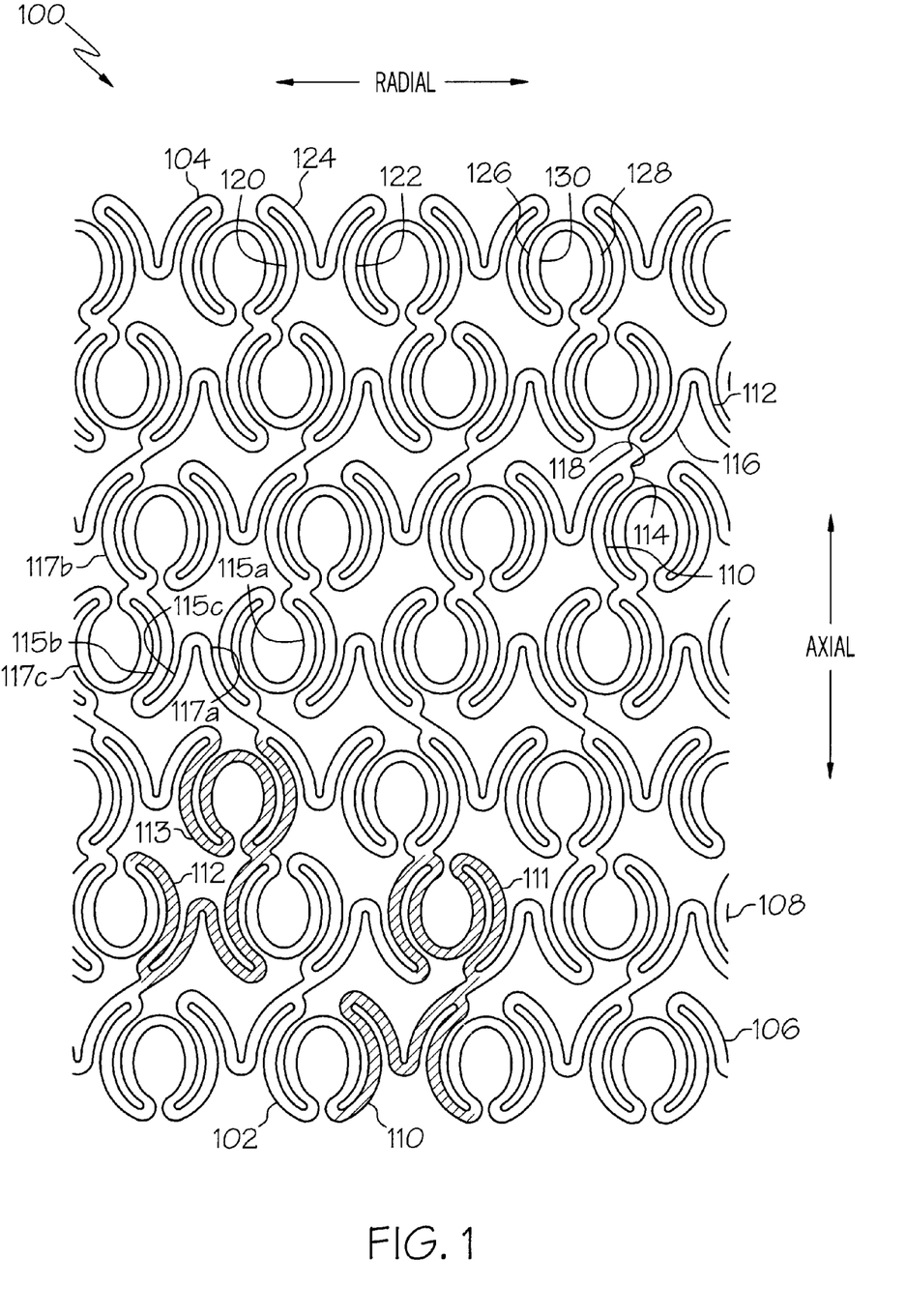
FIG. 1 illustrates a plan view of an expandable stent in accordance with the present invention.
Figure 2A:
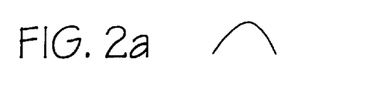
FIGS. 2a–f illustrates various connectors which may be used in the inventive stent disclosed herein.
Figure 2B:
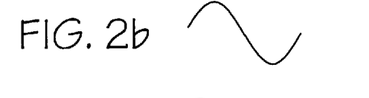
Figure 2C:
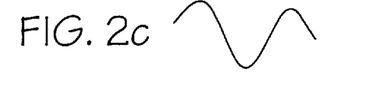
Figures 2D, 2E, 2F:
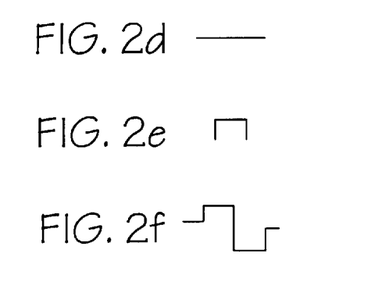

In one embodiment, the invention is directed to a stent such as that shown generally at 100 in FIG. 1. Stent 100, shown as a flat pattern in FIG. 1, has a proximal end 102 and a distal end 104. Stent 100 comprises a plurality of interconnected circumferential bands 106 and 108 with a flow-path therethrough. Bands 106 are comprised of connected convex M-shaped segments 110 (shown highlighted) and bands 108 are comprised of connected convex M-shaped segments 112 (shown highlighted). Convex M-shaped segments 112 are inverted relative to convex M-shaped segments 110. Bands 106 and 108 alternate over the length of the stent and adjacent bands are connected to one another. As shown in FIG. 1, an upper corner 114 of convex M-shaped segment 110 is connected to an upper corner 116 of convex M-shaped segment 112 via connector, 118. Adjacent bands may also be connected by other suitable connectors 118 such as those shown in FIGS. 2a–f. The connectors may extend exclusively in a longitudinal direction or may include a circumferential component as shown in FIG. 1 and as described in copending, commonly assigned U.S. applications Ser. No. 08/511076 and Ser. No. 09/197278. Adjacent bands may be connected by a plurality of connectors as shown in FIG. 1 or by a single connector.

Convex M-shaped segment 110 comprises a first convex outer leg 120, a second convex outer leg 122 and a connector. connecting 124 first convex outer leg 120 and second convex outer leg 122. Inverted convex M-shaped segments 112 similarly comprise a first convex outer leg, a second convex outer leg and a connector connecting the first convex outer leg and the second convex outer leg.

Adjacent convex M-shaped segments in a band are connected by a loop 126 comprising a first portion 128 and a second portion 130. First portion 128 is connected to a first concave leg 120 of a first convex M-shaped segment and second portion 130 is connected to a second concave leg 122 of an adjacent convex M-shaped segment.

Desirably, as shown in FIG. 1, first portion 128 is substantially parallel to first concave leg 120 of the convex M-shaped segment and second portion 130 is substantially parallel to second concave leg 122 of the adjacent convex M-shaped segment.

The invention also contemplates other shaped loops. Moreover, the invention contemplates connecting adjacent M-shaped segments in a band with other types of connectors including any of those shown in FIGS. 2a–f and those described in U.S. application Ser. No. 09/197278. Such connectors may extend in a purely circumferential direction between points on adjacent M-shaped segments in a band, whether at the proximal or distal ends of the first and second legs of an M-shaped segment, the center or anywhere else along the first and second legs. The connectors may also include a longitudinal component.

The invention is also directed to a stent having at least one concave M-shaped segment with concave legs as shown at 111 in FIG. 1. Concave M-shaped segment 111 comprises first and second concave legs connected by a loop portion.

The stent desirably comprises a plurality of concave M-shaped: segments 111 per band with circumferentially adjacent concave M-shaped segments connected one to the other. Adjacent bands are also interconnected.

As shown in FIG. 1, the stent may be constructed and arranged to have overlapping convex and concave M-shaped segments in each bands. In the embodiment shown in FIG. 1, the stent comprises alternating first bands 106 having convex M-shaped segments 110 and second bands 108 having convex M-shaped segments 112 which are inverted and similarly, concave M-shaped segments 111 and second bands 108 having concave M-shaped segments 113. The inventive stents may also be formed of first bands and second bands which do not alternate over the length of the stent. For example, a first portion of the stent may comprise bands having M-shaped segments of one orientation and a second portion of the stent may comprise bands having inverted M-shaped segments.

The invention also contemplates stents formed exclusively of bands of M-shaped segments where the M-shaped segments are identically oriented.

The invention further contemplates stents having bands with differing numbers of convex and/or concave M-shaped segments. For example, a first band may consist of j M-shaped segments and a second band may consist of k M-shaped segments where j is an integer greater than k. Moreover, the stent may comprise different bands having different amplitudes or differing strut widths and/or thicknesses. The stent may be provided with a uniform diameter or may taper.

The invention is also directed to a stent, such as that shown generally at 100 in FIG. 1 where at one of the bands comprises a repeating pattern of three or more substantially parallel interconnected segments 115a–c with a first curvature and three or more substantially parallel interconnected segments 117a–c with a second curvature. One of the segments 115c with the first curvature is connected to one of the segments 117a with the second curvature. Desirably, the first curvature is opposite to the second curvature. Also desirably, the stent comprises a plurality of the bands with each band comprising a repeating pattern of three or more substantially parallel interconnected segments with a first curvature and three or more substantially parallel interconnected segments with a second curvature, one of the segments of the first curvature connected to one of the segments with the second curvature.

Figure 3:
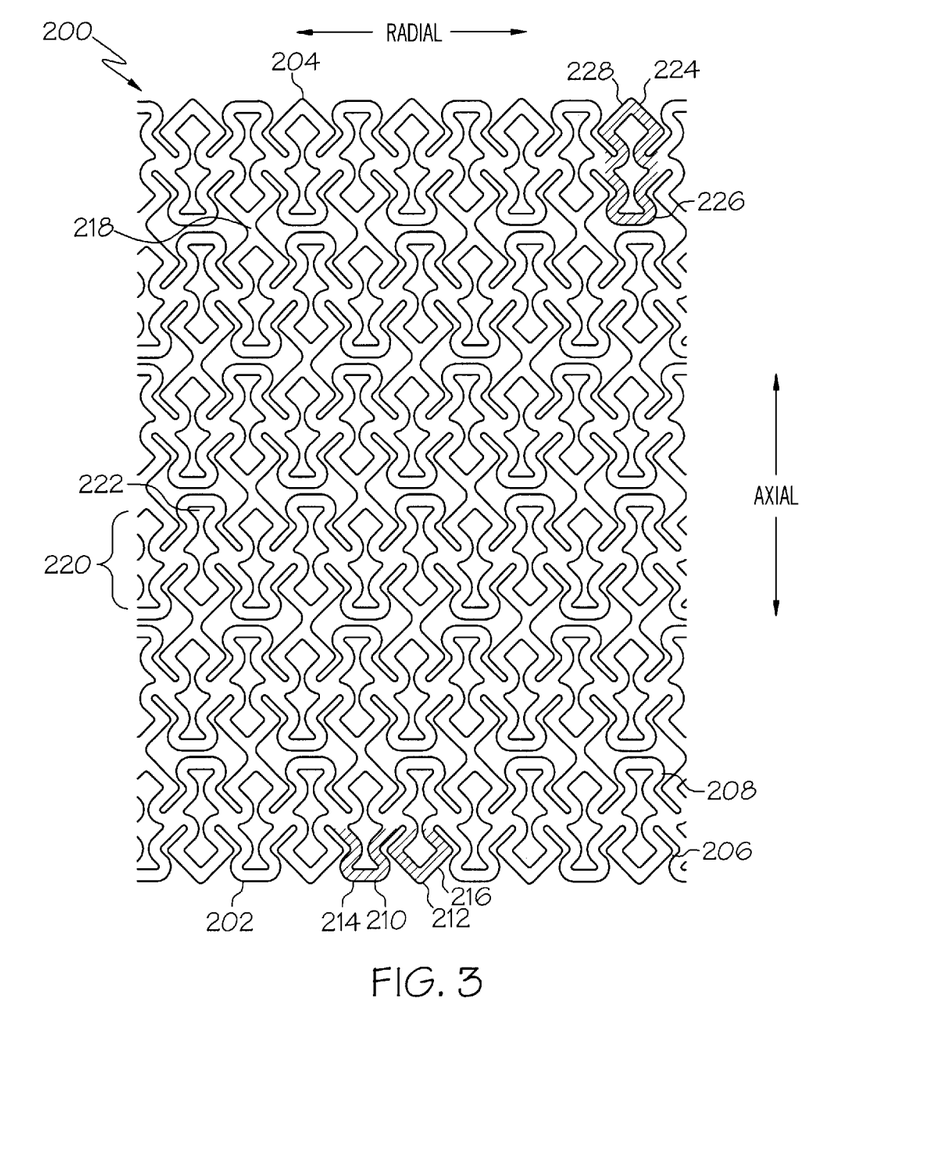
FIG. 3 illustrates a plan view of an expandable stent in accordance with the present invention.

In another embodiment, the invention is directed to a stent such as that shown generally at 200 in FIG. 3. Stent 200, shown as a flat pattern in FIG. 3, has a proximal end 202 and a distal end 204. The stent comprises a plurality of interconnected bands 206 and 208. Bands 206 and 208 are defined by a plurality of alternating first loops 210 (shown shaded) and second loops 212 (shown shaded). First loops 210 include a circumferential portion 214 which is disposed substantially circumferentially and second loops 212 include a substantially arrow-shaped portion 216. Substantially arrow shaped is defined here to be any shape resembling the head of an arrow. Bands 206 and 208 resemble one another but are oppositely oriented. That is, the arrow shaped loops of bands 206. point in the proximal direction and the arrow shaped loops of bands 208 point in the distal direction. Bands 206 and 208 are also 180 degrees out of phase with one another.

Adjacent bands 206 and 208 are joined end-to-end to form a combined band 220. Combined bands 220 have a plurality of openings 222 therein. As shown in FIG. 3, adjacent bands 206 and 208 abut one another. Adjacent bands 206 and 208 may also be connected using any of the connectors shown in FIGS. 2a–f. The connectors may extend entirely in a longitudinal direction or may also include a circumferential component.

Adjacent combined bands are connected end-to-end along the length of the stent via connectors 218. Connectors 218 may also be replaced by any of the connectors shown in FIGS. 2a–f. The connectors may extend entirely in a longitudinal direction or may also include a circumferential component.

The invention is further directed to stents having a single combined band 220, the proximal or distal end of which comprises at least one first loop 210 and at least one second loop 212. Desirably, the first loop 210 is an arrow shaped loop at one end and second loop 212 comprises a substantially circumferential portion 214 at one end. More desirably, the stent comprises at least one combined band 220 having a plurality of first loops 210 and second loops 212 and even more desirably, the first and second loops alternate with one another.

The invention is also directed to a stent such as that shown generally at 200 in FIG. 3, comprising at least one first cell 224 (shown highlighted) having a first end 226 and a second end 228. First end 226 terminates in a circumferential component and second end 228 terminates in an arrow-shaped component opposite first end 226. Desirably, the stent comprises a plurality of interconnected first cells. The first cells may be interconnected circumferentially about the stent in bands and/or longitudinally along the length of the stent. The first cells may be connected longitudinally and/or circumferentially as shown in FIG. 3 or using any of the connecting elements shown in FIGS. 2a–f. The connectors may be exclusively longitudinal or circumferential or may include longitudinal and circumferential components.

As shown in FIG. 3, the orientation of circumferentially adjacent first cells 224 alternate. The first end of every other first cell 224 points in the proximal The invention also contemplates embodiments in which every first cell is identically oriented..

Where the stent comprises a plurality of bands 220 of first cells 224, each band may consist of identically oriented first cells or first cells with alternating orientations. The invention also contemplates providing one or more bands having first cells oriented exclusively in one direction and one or more bands having first cells oriented exclusively in the opposite direction. Such bands may alternate over the length of the stent or may be provided in any other order along the length of the stent.

The invention further contemplates stents having bands 220 with differing numbers of first cells 224. For example, a first band may consist of j first cells and a second band may consist of k first cells where j is an integer greater than k. Moreover, the stent may comprise different bands having different amplitudes or longitudinal lengths or differing strut widths and/or thicknesses. The stent may be provided with a uniform diameter or may taper.

Figure 4:
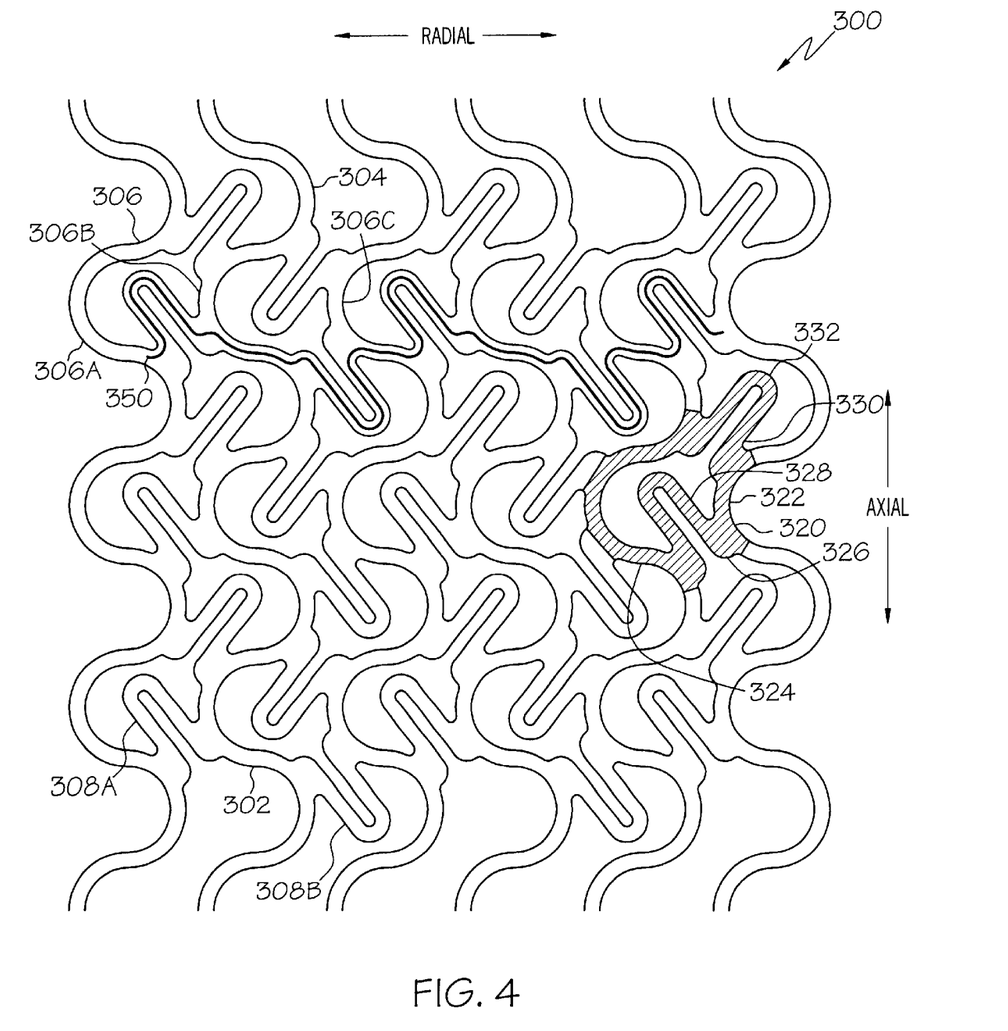
FIG. 4 illustrates a plan view of another inventive stent.

In another embodiment, as shown in FIG. 4, the invention is directed to a stent, shown generally at 300, having a proximal end 302 and a distal end 304. Stent 300 comprises a plurality of serpentine bands 306 extending in a longitudinal direction, including a first serpentine band 306a and a second serpentine band 306b. First serpentine band 306a and second serpentine band 306b are connected by at least one and desirably a plurality of loop members 308a extending in a direction non-parallel to the longitudinal axis of the stent. Longitudinally adjacent first loop members 308a connecting first serpentine band 306a and second serpentine band 306b open toward the proximal end of the stent. Longitudinally adjacent first loop members 308a may be non-parallel to one another, oppositely oriented about the longitudinal axis of the stent as shown in FIG. 4 or may be substantially parallel to one another, as shown in FIG. 5.

Stent 300 further comprises a third serpentine band 306c extending in the longitudinal direction. Third band 306c is adjacent to second band 306b and connected thereto via a plurality of second loop members 308b. Second loop members 308b open toward the distal end of the stent. Longitudinally adjacent second loop members 308b may be non-parallel to one another, oppositely oriented about the longitudinal axis of the stent as shown in FIG. 4 or may be substantially parallel to one another, as shown in FIG. 5.

Figure 5:
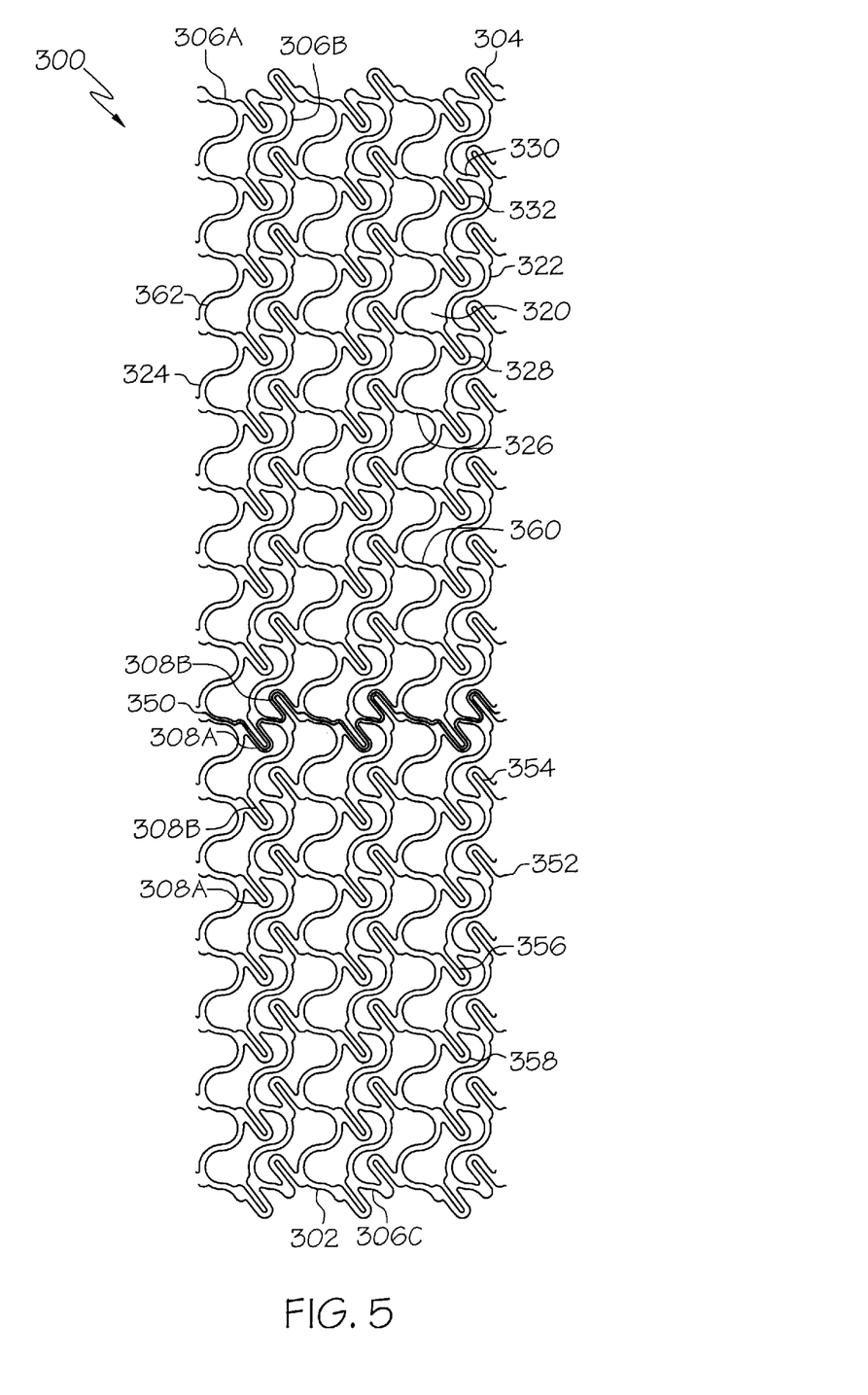
FIG. 5 illustrates a plan view of another inventive stent.

As shown in FIGS. 4 and 5, additional serpentine bands may be present as well, interconnected with loop members as described above.

The invention is also directed to a stent, such as that shown generally at 300 in FIG. 4, comprising at least one first cell 320 (shown highlighted) comprising a first generally longitudinal sidewall 322 desirably having at least one bend therein and a second generally longitudinal sidewall 324 having at least one bend therein. First generally longitudinal sidewall 322 is substantially parallel to second generally longitudinal sidewall 324. Cell 320 further comprises a proximal wall 326 having at least one loop 328 therein and a distal wall 330 having at least one loop 332 therein. Loops 328 and 332 are oriented non-parallel to the longitudinal axis of the stent.

Desirably, the stent comprises a plurality of first cells arranged longitudinally one or more rows along the length of the stent. The first cells are also seen to be arranged circumferentially in bands about the stent. In the embodiment shown in FIG. 4, for each cell, the loop in the proximal wall is non-parallel to the loop in the distal wall. In another embodiment of the invention, as shown in FIG. 5, all of the loops in the proximal walls of the cells and all of the loops in the distal walls of the cells are substantially parallel to one another.

The invention is also directed to stents such as those shown in FIGS. 4 and 5 which are comprised of a plurality of bands 350 (shown highlighted) where each band comprises a plurality of distally directed loops 308b and a plurality of proximally directed loops 308a. Each distally directed loop 308b has an open end 352 and a closed end 354 and each proximally directed loop 308a has an open end 356 and a closed end 358. Desirably, proximally directed loops 308a and distally directed loops 308b are parallel to one another and non-parallel to the longitudinal axis of the stent. The proximally directed loops and the distally directed loops alternate around the band and are connected to one another by first connectors 360 which extend from the open end 356 of the proximally directed loops 308a to the open end 352 of the distally directed loops 308b. First connectors 360 include a circumferential component. Bands which are adjacent one another are connected by one or more second connectors 362 extending therebetween. Second connector 362 desirably has at least one bend therein and more desirably, two bends.

As shown in FIGS. 4 and 5, the proximally directed loops in adjacent bands may be non-parallel with one another or parallel with one another.

The stents of FIGS. 4 and 5 may be provided in a number of variants. For example, the stent may be provided with a uniform diameter or may taper. Also, the width and/or thickness of the serpentine bands and/or connectors may increase or decrease along a portion of the stent.

Figure 6:
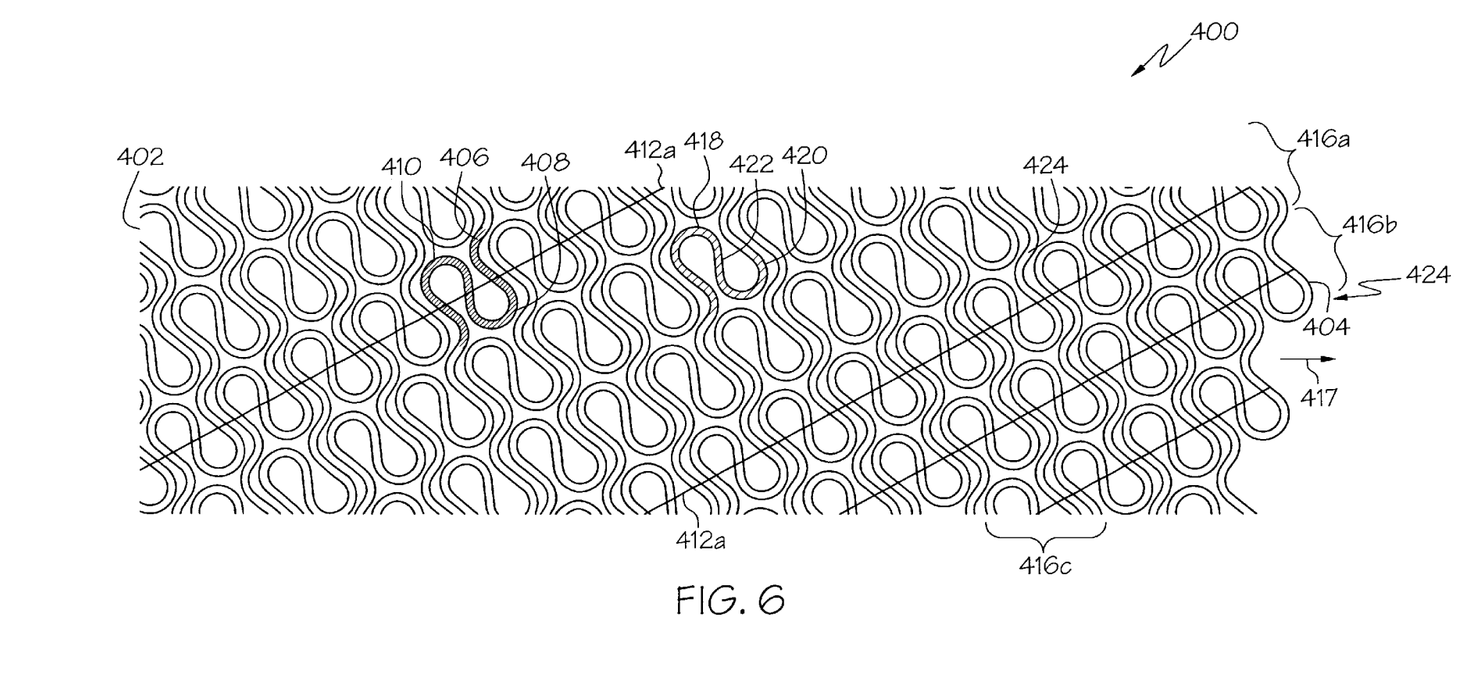
FIG. 6 illustrates a plan view of another inventive stent.

In another embodiment, the invention is directed to a stent such as that shown generally at 400 in FIG. 6. Stent 400 has a proximal end 402 and a distal end 404 and is defined by a structure comprising a plurality of serpentine portions 406 (shown highlighted). Each serpentine portion 406 has at least one peak 408 and one trough 410, desirably disposed at a non-zero angle with respect to the longitudinal axis 414 of the stent. Also desirably, each serpentine portion consists of one peak and one trough although additional peaks and/or troughs may be present.

Serpentine portions 406 may be provided in a variety of shapes. Desirably, however, the serpentine portions will be in the shape shown in FIG. 6, namely, in the shape of a first omega 418 joined side by side with a second omega 420, the second omega inverted relative to the first omega and the first and second omegas having a side 422 in common. The omegas are disposed at a non-zero angle relative to the longitudinal axis of the stent.

At least some of the serpentine portions 406 advance discontinuously along a helical path 412a about a longitudinal axis 414 of the stent to form a discontinuous helical band 416a. Desirably, serpentine portions 406 are arranged to form a plurality of discontinuous helical bands (e.g. 416b, 416c). The stent of FIG. 6 is provided with three such discontinuous helical bands. Fewer or additional discontinuous helical bands may be provided.

As shown in FIG. 6, all adjacent serpentine portions 406 within a discontinuous helical band (416a,b, or c) are separated from one another by gaps. Where the stent comprises a multiplicity discontinuous helical bands, adjacent discontinuous helical bands (for example 416a–c) may optionally be connected to one another at one or more locations 424.

Desirably, as shown in FIG. 6, serpentine portions 406 are connected so as to form a continuous path extending from one end of the stent to the other end of the stent.

Figure 7:
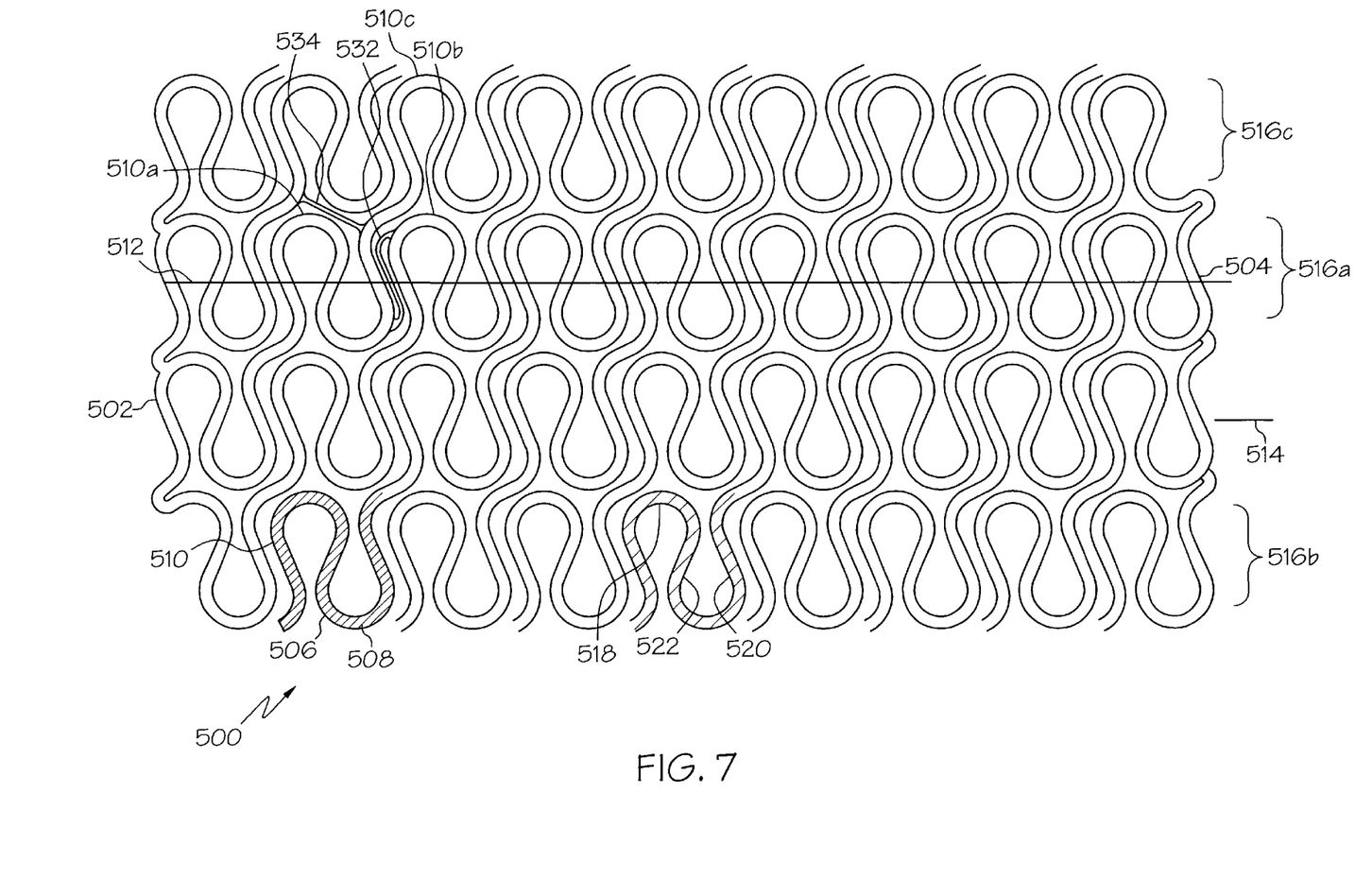
FIG. 7 illustrates a plan view of another inventive stent.

The embodiment of FIG. 6 may also be modified so that discontinuous bands extending in a lengthwise direction are formed as is shown generally in FIG. 7. Stent 500 has a proximal end 502 and a distal end 504 and is defined by a structure comprising a plurality of serpentine portions 506 (shown highlighted). Each serpentine portion 506 has at least one peak 508 and one trough 510, desirably disposed at a non-zero angle with respect to the longitudinal axis 514 of the stent. Also desirably, each serpentine portion consists of one peak and one trough although additional peaks and/or troughs may be present.

Serpentine portions 506 may be provided in a variety of shapes. Desirably, however, the serpentine portions will be in the shape shown in FIG. 7, namely, in the shape of a first omega 518 joined side by side with a second omega 520, the second omega inverted relative to the first omega and the first and second omegas having a side 522 in common. The omegas are disposed at a non-zero angle relative to the longitudinal axis of the stent.

At least some of the serpentine portions 506 advance discontinuously along a longitudinal path 512 about a longitudinal axis 514 of the stent to form a discontinuous bands 516a extending in a lengthwise direction. Desirably, serpentine portions 506 are arranged to form a plurality of discontinuous bands extending in a lengthwise direction (e.g. 516b, 516c). The stent of FIG. 7 is provided with a total of four such discontinuous bands extending in a lengthwise direction. Fewer or additional discontinuous bands extending in a lengthwise direction may be provided.

As shown in FIG. 7, all adjacent serpentine portions 506 within a discontinuous band (516a,b, or c) extending in a lengthwise direction are separated from one another by gaps. Where the stent comprises a multiplicity discontinuous bands extending in a lengthwise direction, adjacent discontinuous bands extending in a lengthwise direction (for example 516a–c) may optionally be connected to one another at one or more locations 524.

Desirably, as shown in FIG. 7, serpentine portions 506 are connected so as to form a continuous path extending from one end of the stent to the other end of the stent.

The stents of FIGS. 6 and 7 and their variants discussed above may be provided with connectors to bridge the gap between adjacent serpentine portions within a given discontinuous helical (or longitudinal) band. As shown in FIG. 7, connector 532 connects serpentine portion 510a to adjacent serpentine portion 510b in discontinuous band 516a extending in a lengthwise direction. Some or all of the gaps within a discontinuous longitudinal (or helical band) may thus be bridged.

Connectors 532 may be straight or curved and may be of the same thickness and/or width as the serpentine portions of the stent or may be of a smaller width and/or thinner.

One or more additional connectors may also be provided to directly connect circumferentially adjacent serpentine portions. An example of such a connector is shown in FIG. 7. Connector 534 extends between circumferentially adjacent serpentine portion 510a and 510c. Connectors 534 may be straight or curved and may be of the same thickness and/or width as the serpentine portions of the stent or may be of a smaller width and/or thinner.

In addition to the stent formation techniques disclosed below, the stents of FIGS. 6 and 7 and their variants may be made by winding a wire in the desired pattern. The ends of the wire may optionally be secured to the stent as shown in FIGS. 6 and 7.

As shown in FIGS. 6 and 7, the invention is also directed to a stent comprising a meandering path of connected serpentine portions 406 (506). Each serpentine portion comprises a first loop portion 408 (508) and a second loop portion 410 (510) which are arranged side-by-side and have a side in common. The first and second loop portions each open in a non-longitudinal direction. Adjacent serpentine portions along the meandering path are connected to one another end-to-end and are displaced longitudinally and circumferentially from one another along the meander path.

The serpentine portions may be arranged substantially helically about a longitudinal axis of the stent as shown in FIG. 6, or in at least one discontinuous band extending in a substantially longitudinal direction as shown in FIG. 7.

The invention is also directed, as shown in FIGS. 6 and 7, to a stent comprising a meandering, substantially helical path of connected serpentine portions. Each serpentine portion comprises first and second loop portions which are arranged side-by-side and have a side in common. The first and second loop portions each open in a non-longitudinal direction. The serpentine portions may be arranged in at least one discontinuous band extending substantially helically about a longitudinal axis of the stent or may be arranged in at least one discontinuous band extending in a substantially longitudinal direction.

In addition to the variation discussed above, the stents of FIGS. 6 and 7 and their variants may have a uniform diameter or may taper. Also, the width and/or thickness of the serpentine portions may increase or decrease along a portion of the stent.

Figure 8:
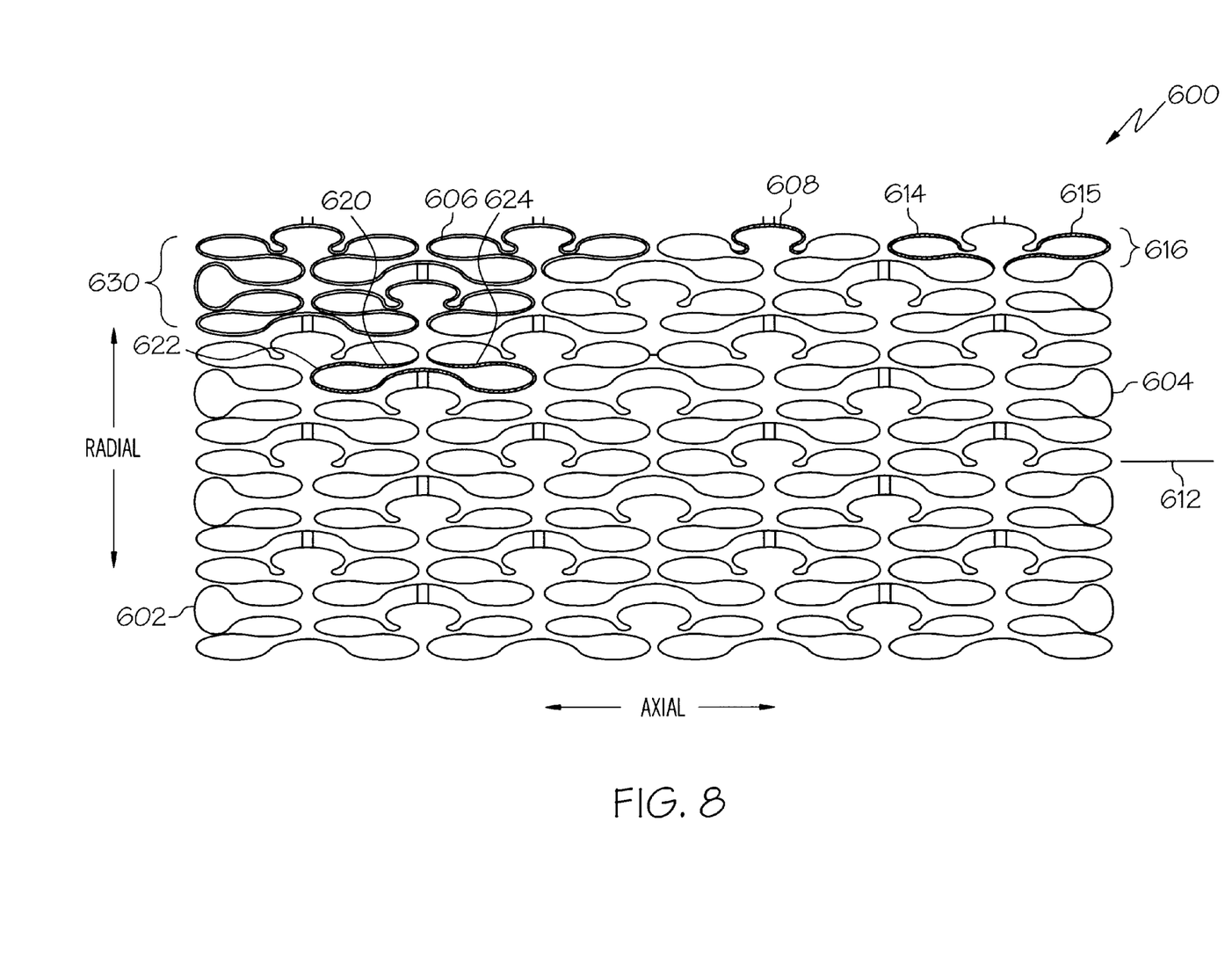
FIG. 8 illustrates a plan view of another inventive stent.

The invention is also directed to a stent such as that shown generally at 600 in FIG. 8. Stent 600 has a proximal end 602, a distal end 604 and a longitudinal axis 612. Stent 600 comprises an omega building block 606 (shown highlighted). Omega building block 606 comprises a circumferentially oriented omega-shaped loop 608 having a proximal end and a distal end, a substantially proximally oriented first lobe 614 extending from the proximal end of omega-shaped loop 608 and a substantially distally oriented first lobe 615 extending from the distal end of omega-shaped loop 608. Desirably, stent 600 comprises a plurality of interconnected omega building blocks 606 arranged in a band 616 extending in a lengthwise direction along the stent. Desirably, longitudinally adjacent omega building block members 606 in the band 616 extending in a lengthwise direction are connected by dual lobe members 620 (shown highlighted). Dual lobe member 620 comprises a substantially proximally oriented second lobe 622 and a substantially distally oriented second lobe 624 connected to the substantially proximally oriented second lobe 622. The substantially distally oriented first lobe 615 of an omega building block 606 is arranged side by side and has a side in common with the substantially proximally oriented second lobe 622 of a dual lobe member 620. The substantially proximally oriented first lobe 614 of a longitudinally adjacent omega building block 606 is arranged side by side and has a side in common with the substantially distally oriented second lobe 624 of the dual lobe member 620.

Desirably, as shown in FIG. 8, the stent comprises a plurality of longitudinally adjacent dual lobe members. More desirably, the stent comprises a plurality of bands extending in a lengthwise direction of omega building blocks.

At least one of the omega shaped loops 606 is connected circumferentially to a circumferentially adjacent dual lobe member 620 between the substantially proximally oriented second lobe and the substantially distally oriented second lobe as shown in FIG. 8. Any of the other connectors shown in FIGS. 2a–2f may also be used. More desirably, each of the omega shaped loops is connected circumferentially to a circumferentially adjacent dual lobe member between the substantially proximally oriented second lobe and the substantially distally oriented second lobe.

The stent may be comprise a plurality of interconnected closed longitudinal strips 630. Each closed longitudinal strip comprises two bands extending in a lengthwise direction of omega building blocks and two bands extending in a lengthwise direction of dual lobe members. The stent shown in FIG. 8 comprises four such longitudinal strips. The inventive stent may comprise fewer longitudinal strips or additional longitudinal strips. Moreover, the longitudinal strips may be modified to have additional bands extending in a lengthwise direction of omega building blocks and bands extending in a lengthwise direction of dual lobe members.

In addition to the various techniques described below, the inventive stent of FIG. 8 and related embodiments may be made by winding a wire in the desired pattern.

Figure 9:
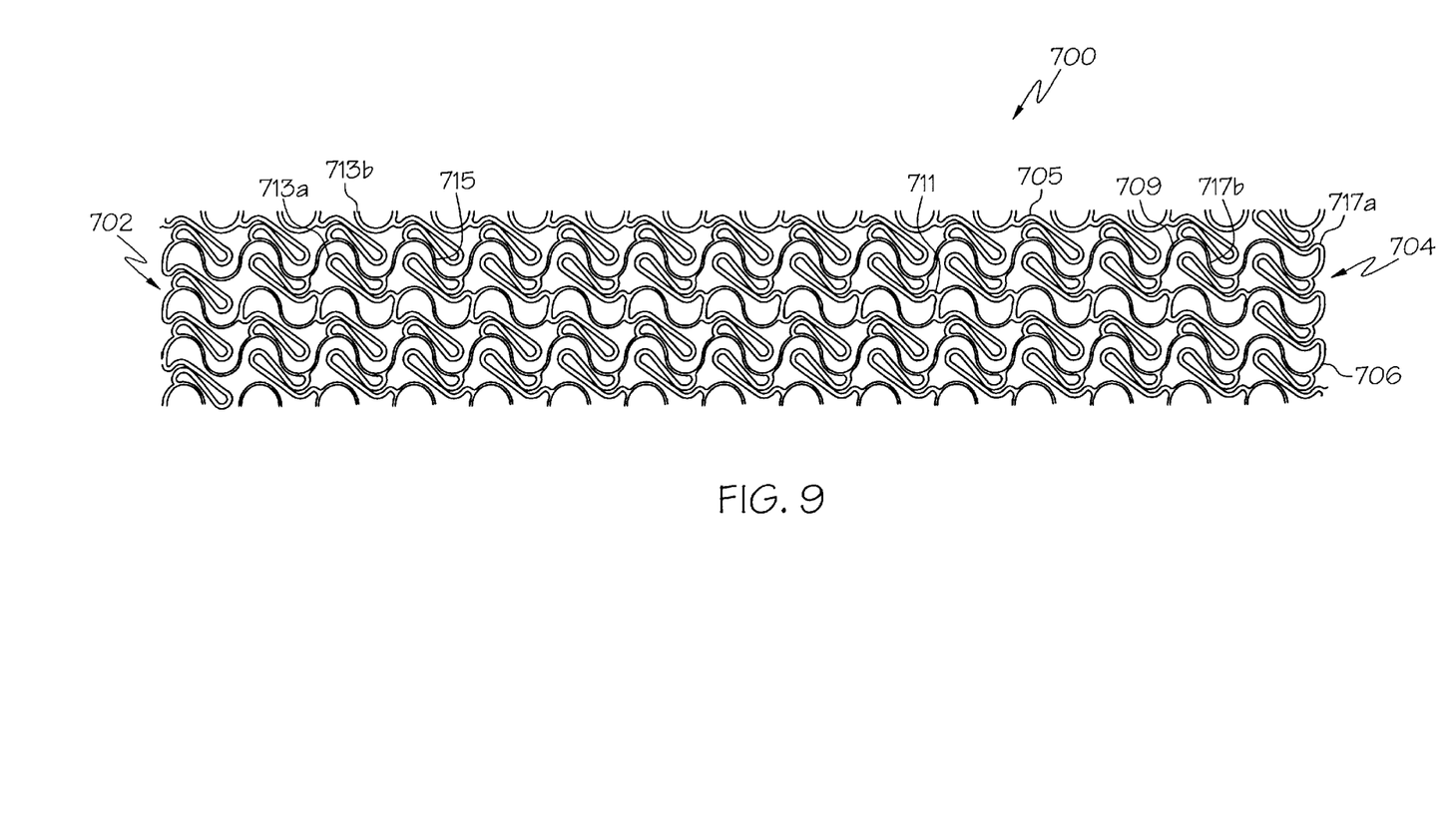
FIG. 9 illustrates a plan view of another inventive stent.

Another embodiment of the inventive stents is shown generally at 700 in FIG. 9 Stent 700, having a proximal end 702 and a distal end 704, comprises a plurality of circumferential bands 705 (one of which is shown highlighted) and a plurality of bands extending in a lengthwise direction 706 (one of which is shown highlighted) which significantly overlap the circumferential bands. The embodiment of FIG. 9 includes four bands extending in a lengthwise direction. More generally, the invention contemplates providing at least one and desirably a plurality of bands extending in a lengthwise direction. Adjacent circumferential bands include two types of connecting regions, a first region where a portion 709 (one of which is shown highlighted) of a band extending in a lengthwise direction extends between adjacent circumferential bands and a second region where adjacent circumferential bands have a segment 711 (one of which is shown highlighted) in common. The circumferential bands are made of a plurality of hairpin curves 713 which alternate in orientation from a distal orientation 713a to a proximal orientation 713b. Circumferentially adjacent hairpin curves are separated and joined together by a curved portion 715 of the band extending in a lengthwise direction. It is noted that the struts forming the bands extending in a lengthwise direction are of a different width than the struts forming the hairpin curves. As such, the circumferential bands are formed in a repeating pattern of two wider struts followed by a narrower strut. The invention also is directed to embodiments in which all of the struts are of the same width.

It is also noted that the stent of FIG. 9 comprises a plurality of circumferential segments each comprising one or more R-shaped segments 717a (one of which is shown highlighted). Desirably, as shown in FIG. 9, the R-shaped segments are disposed at an oblique angle relative to the longitudinal axis of the stent. Also desirably, each band includes both R-shaped segments 717a and inverted R-shaped segments 717b. In the embodiment of FIG. 9, adjacent bands are interconnected by connectors. Also, adjacent R-shaped segments and inverted R-shaped segments in adjacent bands share a portion in common. In accordance with the invention, the inventive stents may have as few as a single R-shaped segment. Desirably, however, one or more R-shaped segments are provided in each band and more desirably, a plurality of such segments are provided.

The invention is also directed to a stent, as shown in FIG. 9, comprising a plurality of circumferential bands 705 which are interconnected by one or more connectors 709 extending between adjacent bands and which further are further connected by one or more segments 711 shared in common between adjacent bands.

Figure 10:
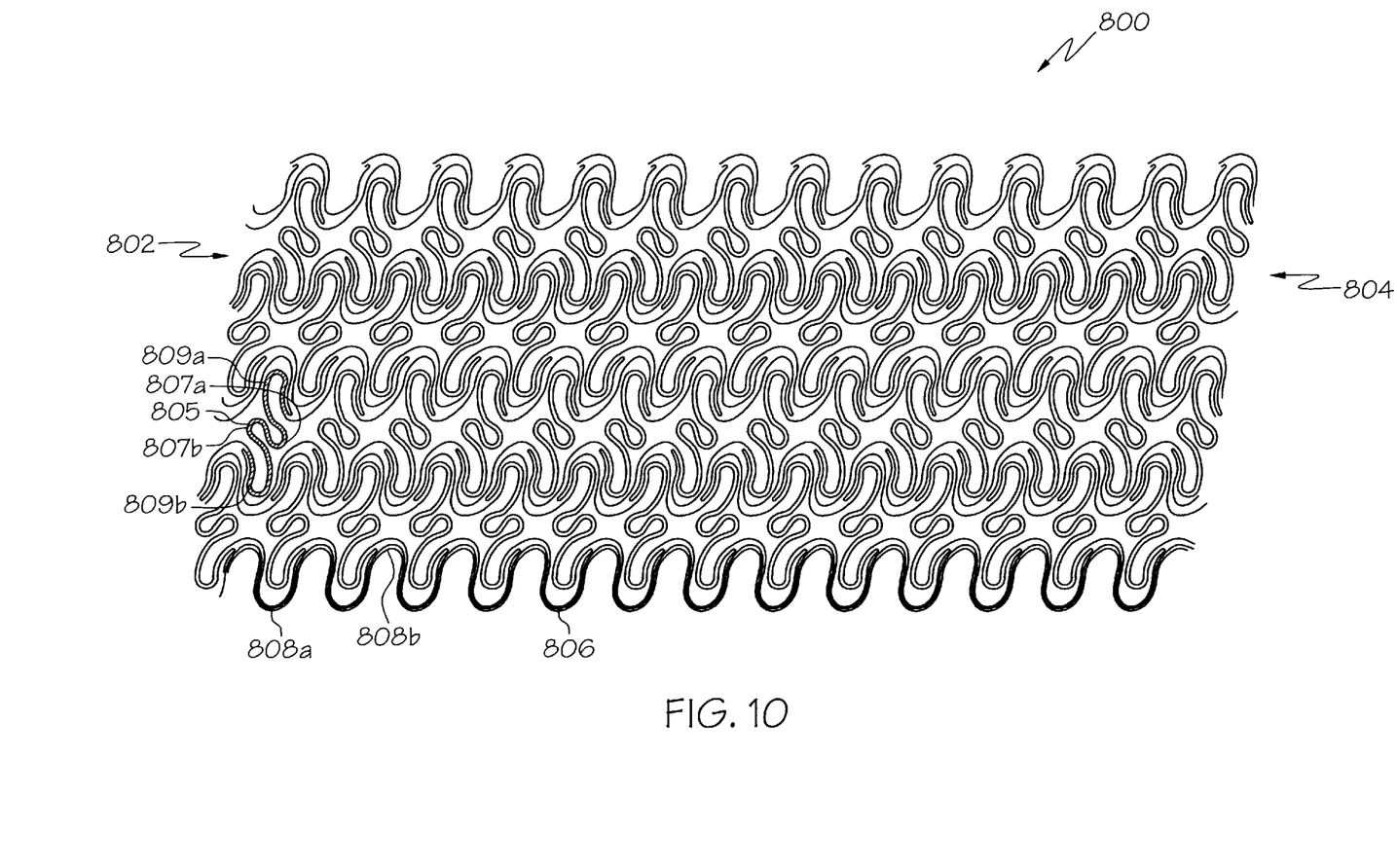
FIG. 10 illustrates a plan view of another inventive stent.

Yet another embodiment of the invention is shown at 800 in FIG. 10. Stent 800, having a proximal end 802 and a distal end 804, comprises a plurality of bands 806 extending in a lengthwise direction (one of which is shown highlighted) of a first strut width interconnected by a plurality of circumferential connectors 805 (one of which is shown highlighted). Bands 806 extending in a lengthwise direction include substantially oppositely directed loops 808a,b. Circumferential connectors 805 desirably have a strut width which is narrower than the strut width of bands 806 extending in a lengthwise direction although the invention also contemplates the struts being of the same width or wider. Circumferential connectors 805 include loop 807a oriented in the distal direction, loop 807b oriented in the proximal direction, and two loops 809a and 809b oriented in opposite substantially circumferential directions. Proximally and distally oriented loops 807a,b are disposed between adjacent bands 806 extending in a lengthwise direction. Substantially circumferentially oriented loops 809a,b are each nested in loops of adjacent bands 806 extending in a lengthwise direction.

More generally, the invention is directed to a stent having one or more bands extending in a lengthwise direction and one or more circumferential members. The circumferential members have two or more loops at least one of which points substantially in the proximal direction and at least one of which points substantially in the distal direction. The circumferential members also include at least two loops which point in opposite, substantially circumferential directions. Desirably, a plurality of longitudinal members are present. More desirably, the longitudinal members also include loops which are oriented in substantially circumferential directions. Even more desirably, at least some of the substantially circumferential loops of the circumferential members are nested within substantially circumferential loops of the longitudinal members. A stent in accordance with this embodiment is shown in FIG. 10.

The invention is also directed to a stent comprising at least one and desirably a plurality of longitudinal elements form a repeat pattern of increasing width followed by a branching of the. longitudinal element with the branch connecting the longitudinal element to an adjacent longitudinal element. The longitudinal element decreases in width at the branch and then increases in width again until another branch point is encountered. A stent in accordance with this embodiment is shown in FIG. 10.

Any of the inventive stents disclosed above may be provided with a uniform diameter or may taper. Also, the width and/or thickness of the various portions of the inventive stents may increase or decrease along a given portion of the stent.

Any of the inventive stents described above as comprising bands may include one or more bands of a first amplitude and one or more bands of a second amplitude different from the first amplitude. Also, those stents described above which are comprised of bands with repeating structural units may include one or more bands with a first number of structural units and one or more bands with a second number of structural units different from the first number. Examples of structural units include M-shaped segments 110 of FIG. 1 and cells 224 of FIG. 3. Bands with different amplitudes and/or numbers of repeating structural units may alternate with one another along the length of the stent. Bands with like and/or numbers of repeating structural units may also be grouped together.

The inventive stents may be manufactured using known stent manufacturing techniques. Suitable methods for manufacturing the inventive stents include laser cutting, chemical etching, electroforming or stamping of a tube. The inventive stents may also be manufactured by laser cutting, chemically etching, stamping or electroforming a flat sheet, rolling the sheet and welding the sheet, by electrode discharge machining, or by molding the stent with the desired design. The inventive stents may also be made by growing or extruding or winding a stent with the inventive patterns.

Any suitable stent material may be used in the manufacture of the inventive stents. Examples of such materials include metals such as stainless steel, tantalum, elgiloy and shape memory metals such as nitinol and shape memory polymers. The inventive stents may also be made of suitable polymeric materials.

The inventive stents may include suitable radiopaque coatings. For example, the stents may be coated with gold or sputtered with tantalum. The stents may also be made directly from a radiopaque material to obviate the need for a radiopaque coating or may be made of a material having a radiopaque inner core.

The inventive stents may also be provided with various bio-compatible coatings to enhance various properties of the stent. For example, the inventive stents may be provided with lubricious coatings. The inventive stents may also be provided with drug-containing coatings which release drugs overtime. Suitable coatings include a sugar or more generally a carbohydrate and/or a gelatin to maintain the stent on a balloon during delivery of the stent to a desired bodily location. Other suitable compounds for treating the stent include biodegradable polymers and polymers which are dissolvable in bodily fluids. Portions of the interior and/or exterior of the stent may be coated or impregnated with the compound. Subjecting the stent to such a treatment also may prevent flaring of the ends of the stent during delivery of the stent. Mechanical retention devices may also be used to maintain the stent on the balloon during delivery.

The inventive stents may be provided in mechanically expandable form, in self-expanding form or as a hybrid of the two. Mechanically expandable stents, in accordance with the invention, may be expanded using any suitable mechanical device including a balloon.

The inventive stents may be used for coronary arteries, peripheral arteries, arteries of the neck and intracranial arteries. More generally, the inventive stents may be used for any vessel of the human body including but not limited to arteries, veins, biliary ducts, urethras, fallopian tubes, bronchial tubes, the trachea and the esophagus.

Suitable stent delivery devices such as those disclosed in U.S. Pat. No. 6,123,712, U.S. Pat. No. 6,120,522 and U.S. Pat. No. 5,957,930 may be used to deliver the inventive stents to the desired bodily location. The choice of delivery device will depend on whether a self-expanding or balloon expandable stent is used.

The inventive stents may also be used as the framework for a graft. Suitable coverings include PTFE and expanded PTFE or any of the materials disclosed in U.S. Pat. No. 5,824,046 and U.S. Pat. No. 5,755,770. More generally, any known graft material may be used.

In addition to the specific embodiments claimed below, the invention is also directed to other embodiments having any other possible combination of the dependent features claimed below taken in conjunction with the independent claims from which they depend.

The above disclosure is intended to be illustrative and not exhaustive. The description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A stent having a proximal end and a distal end, the stent comprising a plurality of interconnected circumferential bands with a flowpath therethrough,
   at least one of the circumferential bands including:
   a plurality of substantially M-shaped segments and
   a plurality of substantially C-shaped segments, each substantially C-shaped segment being connected to at least one substantially M-shaped segment, the substantially C-shaped segments of each circumferential band having a substantially uniform orientation, the plurality of substantially M-shaped segments and the plurality of substantially C-shaped segments defining a repeating pattern of curved strut members, the pattern comprising a plurality of first groups of curved strut members and a plurality of second groups of curved strut members, wherein the first groups and the second groups are alternatingly arranged, each of the first groups comprising at least three consecutive curved strut members having substantially the same curvature, each of the second groups comprising at least three consecutive curved strut members having substantially the same curvature but substantially opposite the curvature of the at least three curved strut members of each of the first groups, at least one curved strut member of each of the first groups being connected to at least one curved strut member of an adjacent second group.

2. The stent of claim 1 wherein the plurality of M-shaped segments are convex M-shaped segments.

3. The stent of claim 2 wherein the convex M-shaped segments comprise a first convex outer leg, a second convex outer leg and a connector connecting the first convex outer leg and the second convex outer leg.

4. The stent of claim 2 wherein the plurality of interconnected circumferential bands comprise a first circumferential band having a plurality of interconnected convex M-shaped segments and a second circumferential band having a plurality of interconnected convex M-shaped segments.

5. The stent of claim 4 wherein adjacent convex M-shaped segments in the first circumferential band are interconnected by at least one substantially C-shaped segment.

6. The stent of claim 4 wherein the convex M-shaped segments of the first circumferential band are inverted relative to the convex M-shaped segments of the second circumferential band.

7. The stent of claim 6 wherein the convex M-shaped segments of the first and second circumferential bands at least partially abut and are connected.

8. The stent of claim 1 wherein the plurality of M-shaped segments are concave M-shaped segments.

9. The stent of claim 8 wherein the concave M-shaped segments comprise a first concave outer leg, a second concave outer leg and a connector connecting the first concave outer leg and the second concave outer leg.

10. The stent of claim 8 wherein adjacent concave M-shaped segments in the at least one of the circumferential bands are interconnected by at least one substantially C-shaped segment extending therebetween.

11. The stent of claim 8 wherein the plurality of interconnected circumferential bands comprise a first circumferential band having a plurality of interconnected concave M-shaped segments and a second circumferential band having a plurality of interconnected concave M-shaped segments.

12. The stunt of claim 11 wherein adjacent concave M-shaped segments in the first circumferential band are interconnected by at least one substantially C-shaped segment extending therebetween.

13. The stent of claim 11 wherein the concave M-shaped segments of the first circumferential band are inverted relative to the concave M-shaped segments of the second circumferential band.

14. The stent of claim 1 wherein the plurality of interconnected circumferential bands comprise a plurality of interconnected convex M-shaped segments and concave M-shaped segments.

15. A stent having a proximal end and a distal end, the stent comprising a plurality of interconnected circumferential bands with a flowpath therethrough, at least one of the circumferential bands comprising a repeating pattern of curved strut members, the pattern comprising a plurality of first groups of curved strut members and a plurality of second groups of curved strut members, wherein the first groups and the second groups are alternatingly arranged, each of the first groups comprising at least three adjacent curved strut members having substantially the same curvature, each of the second groups comprising at least three adjacent curved strut members having substantially the same curvature but substantially opposite the curvature of the at least three curved strut members of each of the first groups, only one curved strut member of each of the first groups being connected to only one curved strut member of an adjacent second group.

16. A stent having a proximal end and a distal end, the stent comprising a plurality of interconnected circumferential bands with a flowpath therethrough, at least one of the circumferential bands comprising a repeating pattern of curved strut members, the pattern comprising a plurality of first groups of connected curved strut members and a plurality of second groups of connected curved strut members, wherein the first groups and the second groups are alternatingly arranged, each of the first groups comprising at least three adjacent curved strut members having substantially the same curvature, each of the second groups comprising at least three adjacent curved strut members having substantially the same curvature but substantially opposite the curvature of the at least three curved strut members of each of the first groups, a first curved strut member of each of the first groups is connected to a first curved strut member of an adjacent second group wherein the connected first curved strut member of each first group and the first curved strut member of the adjacent second group form an omega-shaped segment.

* * * * *